Figure 1:
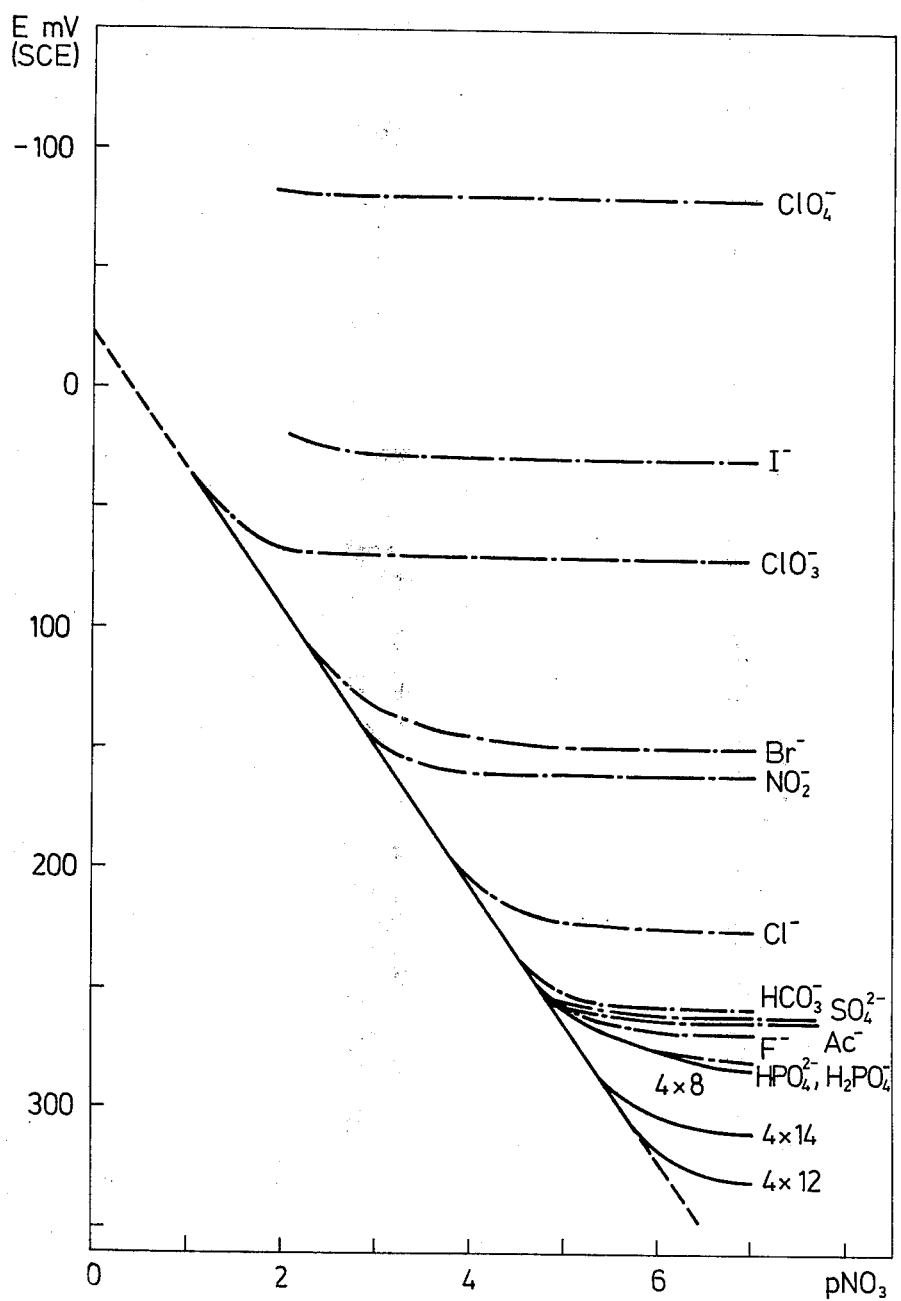

United States Patent [19]

Ibsen Nielsen et al.

[11] 4,059,499

[45] Nov. 22, 1977

[54] NITRATE ION SELECTIVE ELECTRODE

[75] Inventors: Hans Jørgen Ibsen Nielsen, Charlottenlund; Elo Harald Hansen, Lyngby, both of Denmark

[73] Assignee: Bifok AB, Sollentuna, Sweden

[21] Appl. No.: 743,389

[22] Filed: Nov. 19, 1976

[30] Foreign Application Priority Data

Nov. 20, 1975 Denmark .............................. 5217/75

[51] Int. Cl.$^2$ ...................... G01N 27/30; G01N 27/46
[52] U.S. Cl. ................................. 204/195 M; 204/1 T
[58] Field of Search ............. 204/1 N, 195 M; 324/29

[56] References Cited

U.S. PATENT DOCUMENTS

| 3,483,112 | 12/1969 | Ross | 204/195 L |
|---|---|---|---|
| 3,671,413 | 6/1972 | Wise | 204/195 L |

Primary Examiner—G. L. Kaplan
Attorney, Agent, or Firm—Finnegan, Henderson, Farabow & Garrett

[57] ABSTRACT

The present invention relates to an electrode for measuring the nitrate concentration in aqueous solutions. The electrode consists of a container with an internal reference system and a membrane which is a combination of an organic nitrate sensor phase of a quaternary ammonium salt as electroactive material, an organophilic, hydrophobic solvent for the quaternary ammonium salt with substantial viscosity and polyvinyl chloride or polyurethane as non-porous material. The quaternary ammonium salt is chosen from the group consisting of: tetraoctyl ammonium nitrate, tetranonyl ammonium nitrate, tetradecyl ammonium nitrate, tetraundecyl ammonium nitrate, tetradodecyl ammonium nitrate, tetratridecyl ammonium nitrate and tetratetradecyl ammonium nitrate; and the solvent consists of dialkylphthalate or a dialkyladipate of a solubility parameter of 9 ± 2 (cal/cm$^3$)$^{\frac{1}{2}}$.

7 Claims, 3 Drawing Figures

NITRATE ION SELECTIVE ELECTRODE

This invention relates to the construction and use of a membrane containing a quaternary ammonium salt dissolved in a solvent and in a non-porous membrane matrix material which, when enclosed in a container and provided with an inner reference system, permits the manufacture of a nitrate ion selective electrode.

In connection with the study of for example the nitrogen balance in earth systems, plants and water, there is an urgent need for a sensitive and selective method for the determination of nitrate.

During the later years electrodes for the determination of both cations, for example $H^+$, $Na^+$ and $Ca^{2+}$, and anions, for example $Cl^-$, $Br^-$ and $I^-$, have been manufactured. In measurements with ion selective electrodes it is necessary, beyond the sensor electrode, also to use a reference electrode having a potential which can be considered independent on the composition of the aqueous solution in which the measurements are effected, so that the measured potential can be directly referred to the ion species for which the used ion selective electrode is sensitive.

When using a pair of electrodes in which the ion selective electrode is assumed to be sensitive towards the ion A, the relation between the measured potential $E_m$ and the activity of A, $a_A$ is given in the well-known Nernst equation $$E_m = E° + 2.303\, RT/z_A F \cdot \log a_A$$

wherein $E°$ is a constant and $z_A$ is the charge of the ion with its sign, whereas the other symbols are the terms generally used. Since the activity of A and the concentration of A, $c_A$ are interconnected by the activity coefficient $f_A$, the terms $E_m$ and $c_A$ can thus be related to each other by the determination of $f_A$, that is by keeping the ion strength constant in the individual measuring series. The concentration of A in a given unknown solution can therefore be determined on the basis of a calibrating diagram in which $E_m$ is shown in relation to $\log c_A$.

An ion selective electrode is generally built up as a tube within which the inner reference electrode is immersed into the reference solution (liquid or solid) containing a determined activity of the ion species for which the electrode is sensitive (and possibly fixed activities of other chemical compounds), wherein the tube is closed at its lower end by a membrane containing the electroactive material, the composition of said material being the basis on which the selectivity of the electrode towards a given ion species is determined.

Depending on the physical properties of the electroactive material, reference is made to a "solid state" or "liquid state" electrode.

The electroactive materials mentioned in this context for the manufacture of nitrate ion selective electrodes are calculated and exclusively used for incorporation in electrodes of the liquid state category which is also the case for all previously described electroactive materials of nitrate ion selective electrodes. The liquid state electrodes can be classified in two types depending on whether porous or non-porous membranes are used. In the first case the electroactive material (including a possible solvent) is incorporated in a porous material (see for example British patent specification No. 1,197,264), while the electroactive material in the other case is included (possibly together with a solvent) in a non-porous polymer membrane matrix material, for example PVC (polyvinyl chloride), (see for example J. E. W. Davies, G. J. Moody and J. D. R. Thomas, Analyst, 97 (1972) 87–94). Of these two membrane composing methods the inclusion in PVC is the most appropriate and advantageous, because the use of a porous material for the manufacture of membranes, with regard to the securing of the electrochemical circuit, demands continuous leaching of the electroactive material from the membrane out into the solution samples (see for example said British patent specification No. 1,197,264). When using a membrane on a non-porous PVC base this is not only necessary but also irrelevant.

In the manufacture of nitrate ion selective electrodes both of these membrane manufacturing methods have been used although the electroactive materials used in the PVC based membranes were those previously used for the preparation of porous membranes. Nitrate ion selective electrodes based on the last-mentioned technique are described in U.S. Pat. Nos. 3,483,112 and 3,671,413, but these two electrodes have in practice shown to be disadvantageous in that the measured electropotentials in function of time were found to be highly variable and often lacking in systematic tendencies. This can be ascribed to the fact that a wash-out of the electroactive material from the membrane takes place. Beyond the fact that a potential of high variability in time is obtained, the washing out will also result in that the electrode loses its capacity of functioning as a nitrate ion selective electrode (see for example the above-mentioned reference to J. E. W. Davies et al, Analyst, 97 (1972) 87–94).

Like all other ion selective electrodes the nitrate ion selective electrodes are more or less affected by other ion species (see the above-mentioned Nernst equation), and here especially by other anions, but since these interferences can often either be neglected or masked off in different ways, the practical use of the hitherto developed nitrate ion selective electrodes has primarily been limited by the erratic variations of the $E°$ value, which is ascribed to the electroactive material of the membrane. It has therefore been the object of the preparation of the nitrate ion selective electrodes herein described to produce a membrane, the characteristics of which will lead to the production of electrodes having electrode potentials which remain as stable as possible in time, i.e. which in practice will show some $E°$ values which are constant in time. It is a further object of the present invention that said electrodes, beyond maintaining all the selectivity parameters compatible with the hitherto described nitrate ion selective electrodes, should allow a lowering of the lower limit of sensitivity thus leading to a widening of the dynamic measuring range compared with all previously described nitrate ion selective electrodes.

Figure 2:
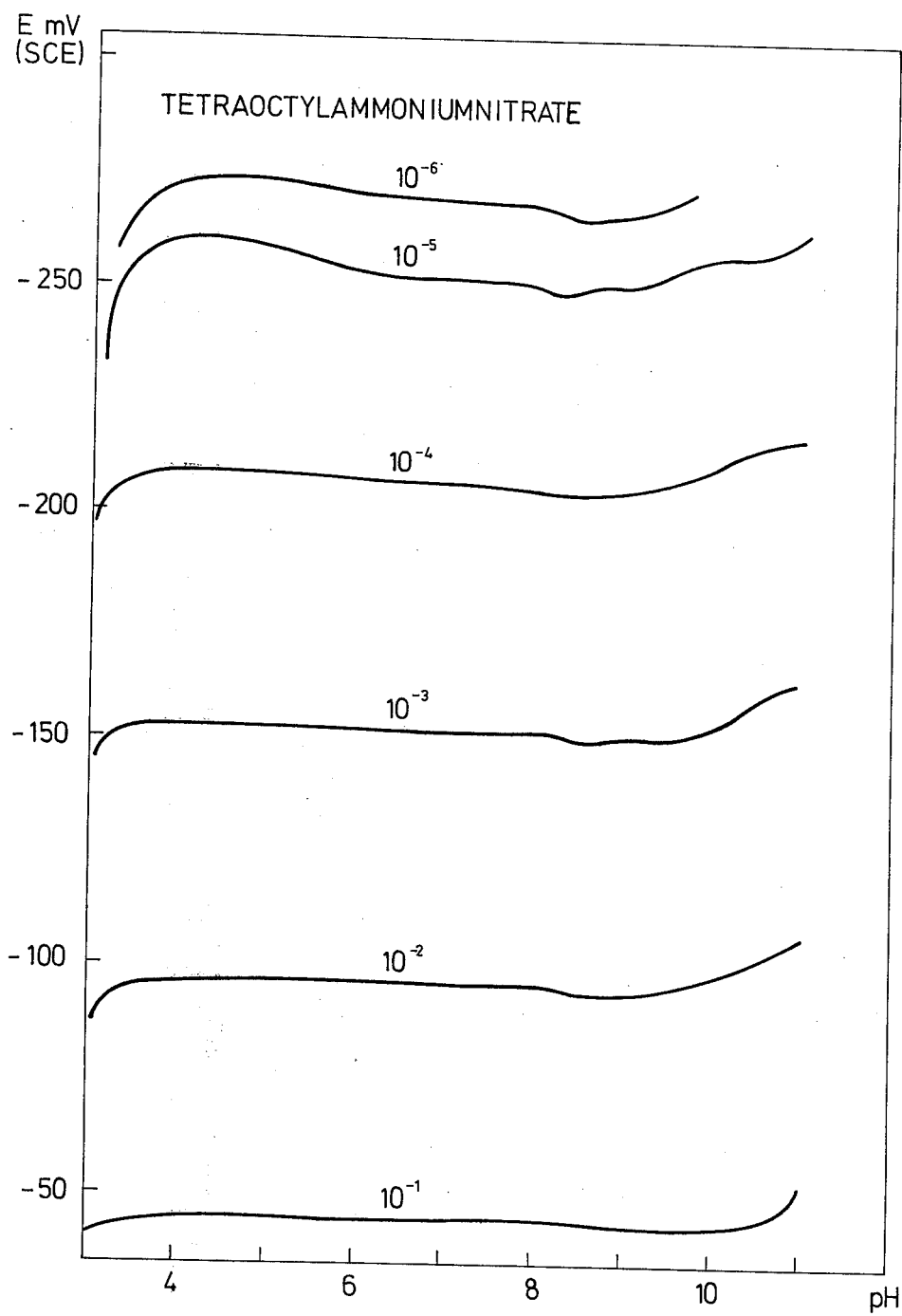
Figure 3:
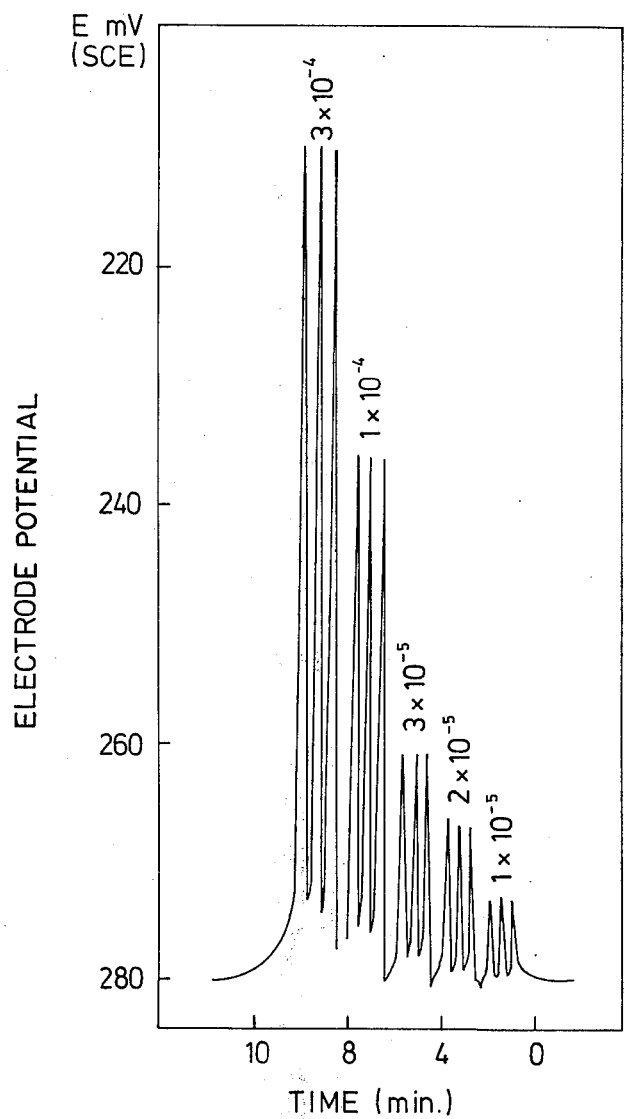

The invention will be described in the following with reference to the accompanying drawings, in which FIG. 1 shows calibration curves for electrodes according to the invention, FIG. 2 shows pH potential diagrams for an electrode according to the invention at different nitrate ion test concentrations, and FIG. 3 shows the electrode signals obtained at the injection of $NaNO_3$ solutions of different concentrations.

The lower limit of sensitiveness of a liquid state electrode is dependent on the coefficient of distribution of the electroactive material between the membrane phase and the aqueous test phase in which the coefficient of distribution for the quaternary ammonium compounds mentioned herein are identical with the ratio of distribution, except at extremely high pH values. Assuming that there are no complex producing species in the membrane, it can be shown by thermodynamic calculations that the coefficient of distribution K between the membrane phase and the aqueous phase can be expressed by the following formula $$-RT \cdot \ln K = V_e V_m \cdot ((d_e - d_m)^2 - (d_e - d_{aq})^2)$$

wherein $V$ indicates the volume ratio, $d$ the solubility parameter measured in $(cal/cm^3)^{\frac{1}{2}}$, and the index $e$ refers to the electroactive material, the index $m$ to the membrane material (i.e. the polymer membrane matrix material and, optionally, the solvent) and the index $aq$ to the aqeous phase. Thus in order to obtain a K value which is as high as possible, the difference $(d_e - d_m)$ must be as small as possible, preferably equal to zero, while the difference $(d_e - d_{aq})$ should be as great as possible. Since the polymer membrane matrix materials most suitable for the production of membranes have a $d$ value of about 9.5, optimal distribution conditions are thus (cf. the above equation) obtained in the production of the ion selective electrode membranes by using electroactive materials as well as solvents which each have $d$ values as close to 9.5 as possible. Since the $d$ value for the electroactive materials mentioned herein, which materials consist of symmetrical quaternary ammonium compounds $R_4N^+$ where R indicates an organic substituent, normally an aliphatic carbon chain, is a function of the number of carbon atoms in the R chain, it can be shown that the distribution ratio K (which is larger than 1 only for chains containing more than 5 carbon atoms) becomes optimal for a carbon chain which is as long as possible. Since the selectivity conditions, however, are practically independent of the length of the carbon chains, these will in practice determine the upper limit for the length of the carbon chains, nothing being attained by lowering the nitrate ion detection limit per se if this never can be attained because of interfering species. In the production of pure quaternary ammonium compounds the synthesis work also becomes unproportionally more difficult the longer the carbon chain is. In the production of the membranes described herein it was found in practice to be neither advantageous nor appropriate to use quaternary ammonium compounds with longer carbon chains than tetradecyl.

As a consequence the following electroactive materials have been produced in pure form and incorporated in membranes for use in the composition of nitrate selective electrodes: Tetraoctyl ammonium nitrate, tetranonyl ammonium nitrate, tetradecyl ammonium nitrate, tetraundecyl ammonium nitrate, tetradodecyl ammonium nitrate, tetratridecyl ammonium nitrate and tetratetradecyl ammonium nitrate.

The membranes referred to in this context were prepared according to the methods previously described by J. Ruzicka et al (J. Ruzicka, E. H. Hansen and J. Chr. Tjell, Anal, Chim. Acta, 67 (1973) 155-178) in that 75 mg PVC powder, 180 mg solvent for PVC and 10 mg of the above-mentiond quaternary ammonium nitrate compounds were dissolved in 5 ml tetrahydrofurane. This solution was used for casting a master membrane, the solution being poured into a 26 mm glass ring placed on a glass plate whereafter the tetrahydrofurane was allowed to evaporate slowly. When the membrane after about 24 hours appeared to be dry it was turned over so that the tetrahydrofurane possibly remaining on the underside could evaporate. By this procedure a 0.3 mm thick membrane was obtained from which five to six membranes each having a diameter of 6 mm could be cut out. By means of a 4% solution of PVC in tetrahydrofurane these membranes were then glued to a hollow cylinder (the electrode member of 110 mm length and 7 mm inner diameter prefabricated in either PVC or plexiglass) whereafter about 3 ml of the inner reference solution were poured into the inner space of the cylinder, said reference solution consisting of a mixture of 0.01 M sodium chloride and 0.01 M sodium nitrate. Finally a reference electrode of Ag/AgCl was immersed into the solution, said electrode having a threaded head fitting into a thread in the forward portion of the electrode member. The nitrate ion selective electrode thus assembled was then ready for use although it was found appropriate for obtaining optimal electrode characteristics to condition the electrodes by placing them for about 24 hours in a 0.1 sodium nitrate solution.

EXAMPLE I

The use of nitrate ion selective electrodes having membranes including tetraoctyl ammonium nitrate, tetradodecyl ammonium nitrate and tetratetradecyl ammonium nitrate, respectively, in PVC with dibutylphthalate as a solvent for the determination of the calibration diagrams and for the determination of the selectivity coefficients $k_{NO_3,x}$ of these electrodes together with the use of the fixed interference method.

Each electrode was calibrated by measuring the equilibrium potential (against a saturated calomel electrode, SCE) wherein the electrode pair connected to a potentiometer was successively immersed into a series of 50 ml standard solutions of sodium nitrate (in the range of concentration $10^{-1}$ to $10^{-7}M$) prepared according to the common dilution technique. The pH in all solutions was about 7. In each case the equilibrium potential established itself within a few seconds. The calibration curves obtained are shown in FIG. 1, wherein the E° values of the three nitrate electrodes, which as expected were not exactly the same, were adjusted for graphic reasons to the same E° value. From FIG. 1 it can be seen that the lower nitrate ion sensitivity limit decreases with increasing length of the carbon chain of R (cf. the expression for the distribution coefficient K shown on page 6). The reason why the order of succession between the electrodes, prepared with tetradodecyl ammonium nitrate and tetratetradecyl ammonium nitrate, respectively, seem to be the reverse of that postulated on the basis of the distribution coefficient, is that it was impossible despite great efforts to produce absolutely pure tetratetradecyl ammonium nitrate. This was further confirmed by the pH potential curves established for the separate single electrodes of which an example is shown in FIG. 2, i.e. for the electrode using a membrane comprising tetraoctyl ammonium nitrate as electroactive material, wherein the potential of the nitrate electrode (versus SCE) as a function of pH is shown for nitrate ion sample concentrations within the range of $10^{-1}$ to $10^{-6}$ M.

The selectivity coefficient $k_{NO_3,x}$ were measured by the fixed reference method recommended by IUPAC (see IUPAC, Information Bulletin, Appendices on Provisional Nomenclature, Symbols, Units and Standards, No. 43, January 1975) using in each case a fixed interference concentration of the species X to $10^{-2}$ M. The results obtained are represented in FIG. 1 wherein the different $k_{NO_3,X}$ values where $k_{A,B}$ is defined by the extended Nernst equation $$\overline{E}_m = E^* + 2{,}303\, RT/z_A F \cdot \log (a_A + k_{A,B} a_B^{z_A/z_B})$$

are found by extrapolating the rectilinear portions of the interference curve for X onto the intersection with the nitrate ion calibrating curve. Thus from FIG. 1 it appears immediately that $k_{NO_3,Cl} = 10^{-2,35}$ while the value of $k_{NO_3,NO_2}$ is $10^{-1,17}$.

The measured selectivity coefficients are, as expected, practically independent of the length of the carbon chains in the quaternary ammonium salt which acts as the electroactive material.

EXAMPLE II

The use of a nitrate ion selective electrode provided with a membrane comprising tetraoctyl ammonium nitrate in PVC with dibutylphthalate as a solvent, in a continuous flow system.

In this case the nitrate electrode, together with a calomel reference electrode, was incorporated in the flow system described by Hansen and Ruzicka (see U.S. patent application Ser. No. 613,275 filed Sept. 15, 1975 now U.S. Pat. No. 4,022,575) which in the actual experimental form consisted of a peristaltic pump accommodating a hose through which a solution of a carrier electrolyte consisting of $10^{-3}$ M sodium fluoride (carrier solution) was pumped with a rate of 9.3 ml/min., the hose thereafter being connected to a system of polyethylene hoses (inner diameter 1.0 mm) including an injection unit, through which system the sample solution of nitrate salt could be introduced by means of a 1.0 ml syringe followed by a 1 m mixing coil from which the aqueous flow was then led through an inlet into a measuring cell containing the two electrodes, and through an outlet of the cell to an outlet. The measuring cell consisted of an inclined plexiglass receptacle in which a constant liquid level could be maintained by the location of the inlets and outlets.

As long as the pure carrier electrolyte solution was pumped through the system a constant potential was registered which was determined by the value of $k_{NO_3,F}$ but as soon as an aqueous sample solution of nitrate (sample volume 0.2 ml) was introduced through the injection unit this was registered by the electrode pair of the measuring cell via a potentiometer and a recorder showing that the electrode response received in the form of a peak was proportional to the logarithm of the concentration of the introduced nitrate solution. In this way the nitrate electrode was calibrated by injection of sodium nitrate solutions in the range of concentration from $10^{-5}$ to $3 \cdot 10^{-4}$ M. The results are indicated in FIG. 3. The calibration curve which could be constructed on the basis thereof was, within the measured range, practically identical with that shown in FIG. 1 thus indicating that, when used under said conditions, the electrode not only reaches its equilibrium potential within very short time but also, as a result of its short response time, permits the use of electrodes with the membranes described in the system as defined in the above-mentioned U.S. Pat. No. 4,022,575, thus disclosing not only a reproducibility hitherto unattained for this type of electrodes but also an unusually short response time.

It should finally be mentioned that in the preparation of the membranes comprising quaternary ammonium salts as described herein it is not essential to start from the nitrate salts of the ammonium compounds concerned, but preliminary also for example the bromide salts of the compounds can be incorporated provided these membranes are thereafter reasonably conditioned for about 24 hours in a $10^{-1}$ M aqueous solution of sodium nitrate, whereby the electroactive material is nevertheless transformed into the corresponding nitrate salt, due to ion exchange.

Although some typical employments and embodiments of the invention have been described in the foregoing and illustrated in the accompanying drawings the invention can be varied and modified as to composition, material and range of use within the scope of the appended claims.

What we claim is:

1. An electrode for measuring the concentration of nitrate ions in aqueous solutions comprising a container embodying an internal reference system and a non-porous polymer membrane mounted upon said container, said membrane comprising a combination of an electroactive material, a solvent and a non-porous polymeric membrane matrix material; wherein said electroactive material is organic nitrate ion sensitive and comprises a quaternary ammonium salt selected from the group consisting of: tetraoctyl ammonium nitrate, tetranonyl ammonium nitrate, tetradecyl ammonium nitrate, tetraundecyl ammonium nitrate, tetradodecyl ammonium nitrate, tetratridecyl ammonium nitrate and tetratetradecyl ammonium nitrate; wherein the solvent is a liquid of substantial viscosity and is a solvent for said quaternary ammonium salt, said solvent consisting of a dialkylphthalate or a dialkyladipate of a solubility parameter of $9 \pm 2$ $(cal/cm^3)^{\frac{1}{2}}$ and being substantially organophilic and hydrophobic; and wherein the polymer membrane matrix material is a non-porous polymer membrane matrix material selected from the group consisting of polyvinylchloride and polyurethane.

2. An electrode provided with a membrane according to claim 1, in which said solvent is dibutylphthalate.

3. An electrode provided with a membrane according to claim 1, in which said nitrate ion sensitive quaternary ammonoum salt consists of tetraoctyl ammonium nitrate and said solvent is dibutylphthalate.

4. An electrode provided with a membrane according to claim 1, in which said nitrate ion sensitive quaternary ammonium salt is tetradodecyl ammonium nitrate and said solvent is dibutylphalate.

5. An electrode provided with a membrane according to claim 1, in which the concentration of said quaternary ammonium salt in said solvent is approximately 5% (w/w).

6. An electrode provided with a membrane according to claim 1, in which said non-porous polymer membrane matrix material is polyvinylchloride.

7. An electrode provided with a membrane according to claim 1, in which said non-porous polymer membrane matrix material is polyurethane.

* * * * *